(12) United States Patent (10) Patent No.: US 7,740,661 B2
Baratz et al. (45) Date of Patent: Jun. 22, 2010

(54) RADIAL HEAD IMPLANT APPARATUSES AND METHODS

(75) Inventors: Mark Baratz, Pittsburgh, PA (US); Mark Cohen, Chicago, IL (US); Robert J. Ball, Eden Prairie, MN (US); Vince Van Donck, San Diego, CA (US); Eric S. Reindel, Encinitas, CA (US); Corey Wilson-Wirth, San Diego, CA (US)

(73) Assignee: Integra Lifesciences Corporation, Plainsboro, NJ (US)

( * ) Notice: Subject to any disclaimer, the term of this patent is extended or adjusted under 35 U.S.C. 154(b) by 447 days.

(21) Appl. No.: 11/210,147

(22) Filed: Aug. 23, 2005

(65) Prior Publication Data

US 2006/0142866 A1 Jun. 29, 2006

Related U.S. Application Data

(60) Provisional application No. 60/603,799, filed on Aug. 23, 2004.

(51) Int. Cl.
*A61F 2/38* (2006.01)

(52) U.S. Cl. .................................................. 623/20.11

(58) Field of Classification Search ........ 623/23.45–47, 623/23.21–23, 23.28, 23.4–42, 23.15, 23.18, 623/23.44, 22.46, 20.11–13; *A61F 2/42*
See application file for complete search history.

(56) References Cited

U.S. PATENT DOCUMENTS

| | | | | |
|---|---|---|---|---|
| 4,224,695 A | * | 9/1980 | Grundei et al. | 623/20.12 |
| 4,384,373 A | * | 5/1983 | Sivash | 623/23.45 |
| 4,955,916 A | * | 9/1990 | Carignan et al. | 623/21.16 |
| 5,011,497 A | * | 4/1991 | Persson et al. | 623/23.41 |
| 5,147,386 A | * | 9/1992 | Carignan et al. | 623/21.16 |
| 5,702,457 A | * | 12/1997 | Walch et al. | 623/19.13 |
| 5,702,470 A | | 12/1997 | Menon | |
| 5,733,292 A | * | 3/1998 | Gustilo et al. | 606/88 |
| 5,782,923 A | * | 7/1998 | Engelbrecht et al. | 623/20.13 |
| 5,879,395 A | * | 3/1999 | Tornier et al. | 623/20.13 |
| 5,989,290 A | * | 11/1999 | Biedermann et al. | 623/17.11 |
| 6,059,832 A | | 5/2000 | Menon | |
| 6,270,529 B1 | * | 8/2001 | Terrill-Grisoni et al. | 623/20.11 |

(Continued)

*Primary Examiner*—Bruce E Snow
(74) *Attorney, Agent, or Firm*—Jenkins, Wilson, Taylor & Hunt, P.A.

(57) ABSTRACT

Radial head implant apparatuses and methods are provided in accordance with the subject matter disclosed herein wherein a shaft and a head portion can be axially movable within a stem portion. In one embodiment, a radial head implant can include a head portion for articular engagement with a humerus bone, a stem portion for engagement with a radius bone, and a shaft for engagement with the stem portion. The head portion can include an upper surface for engaging the humerus bone. The stem portion can have an axial opening for receiving at least a portion of the shaft, and a collar can be disposed around the stem portion at a proximal end thereof. An upper portion of the shaft can be configured for engaging the head portion, while a lower portion of the shaft can be elongated and cylindrical for axially fitting into and moving within the axial opening of the stem portion. Other embodiments are also disclosed for axial movement for a radial head implant. Various structures are disclosed for locking the shaft in position within the stem portion.

5 Claims, 14 Drawing Sheets

U.S. PATENT DOCUMENTS

| | | |
|---|---|---|
| 6,306,171 B1 | 10/2001 | Conzemius |
| 6,361,563 B2 | 3/2002 | Terrill-Grisoni et al. |
| 6,454,810 B1 * | 9/2002 | Lob ........................ 623/23.47 |
| 6,656,225 B2 * | 12/2003 | Martin .................... 623/20.12 |
| 6,709,459 B1 | 3/2004 | Cooney, III et al. |
| 6,811,568 B2 * | 11/2004 | Minamikawa ............ 623/21.15 |
| 6,890,357 B2 * | 5/2005 | Tornier .................... 623/20.12 |
| 2004/0243243 A1 * | 12/2004 | Tornier .................... 623/20.12 |

* cited by examiner

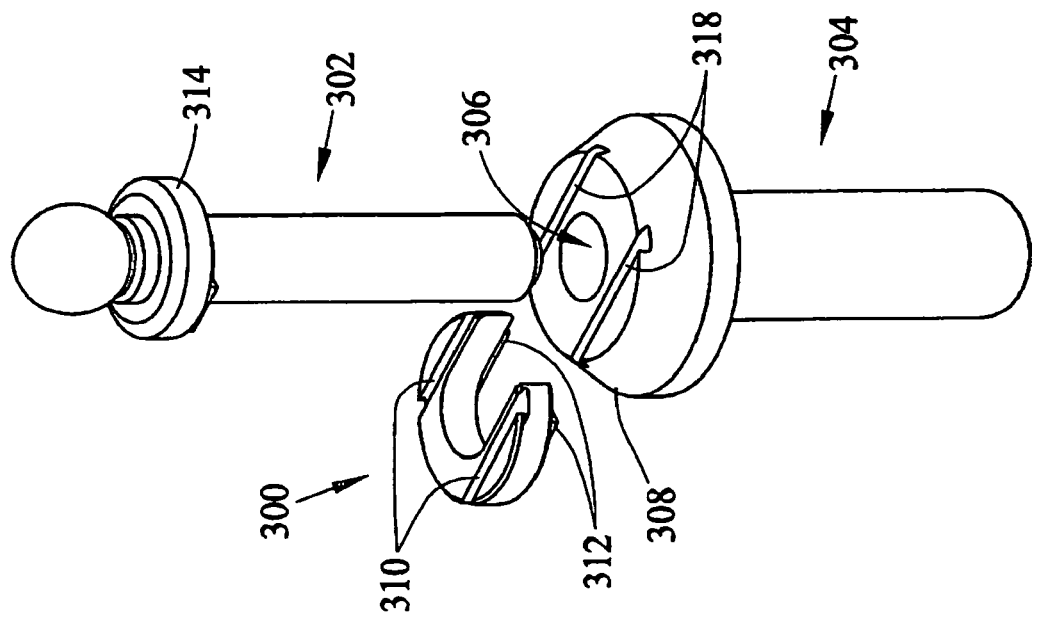
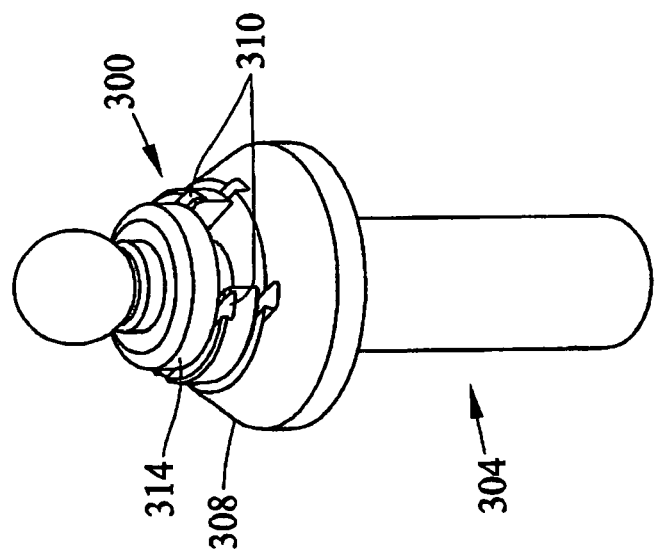
FIG. 13B
FIG. 13A

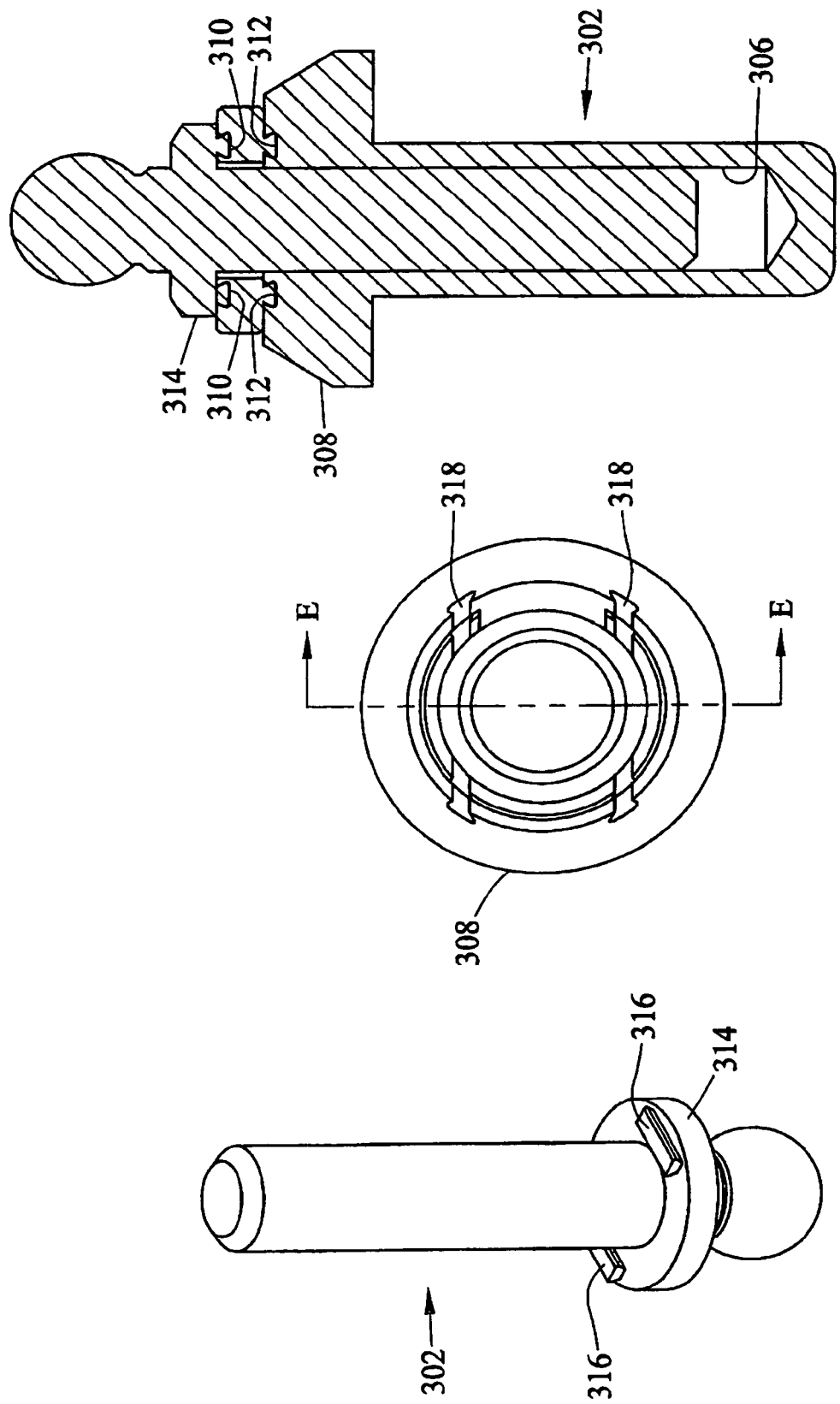

RADIAL HEAD IMPLANT APPARATUSES AND METHODS

RELATED APPLICATION

This application claims the benefit of U.S. Provisional Patent Application Ser. No. 60/603,799, entitled Radial Head Implant Apparatuses and Methods, filed Aug. 23, 2004, the disclosure of which is incorporated herein by reference in its entirety.

TECHNICAL FIELD

The presently disclosed subject matter relates generally to orthopedic apparatuses and methods, and more particularly to orthopedic apparatuses and methods for treating fractures of the radial head.

BACKGROUND ART

Fractures of the radial head account for two to five percent of all adult fractures and are typically treated with a variety of surgical and non-surgical options depending upon the severity of the injury. For example, surgical options for more severe injuries to the radial head can include open reduction with internal fixation (ORIF), radial head resection, hemi-arthroplasty of the radial head, and total elbow replacement. Hemi-arthroplasty of the radial head involves resecting the fractured and damaged radial head and replacing the natural articulation with an artificial one by use of an implant. The implant articulates with the natural cartilage surface of the capitulum of the distal humerus. Over time, radial head implant apparatuses and methods utilized for treatment have evolved to continuously improve surgical outcomes.

As can be appreciated by those of skill in the art, indications which can be associated with the use of radial head implant apparatuses and methods can include:
 Comminuted radial fracture with or with associated elbow instability;
 Comminuted radial fracture with associated rupture of the interosseous membrane, the Essex-Lopresti lesion;
 Post-traumatic arthritis involving the radiocapitellar or proximal radioulnar joint;
 Primary osteoarthritis involving the radiocapitellar joint or proximal radioulnar joint;
 Rheumatoid arthritis involving the radiocapitellar joint or proximal radioulnar joint; and
 Revision of a failed radial head prosthesis.

It is well known that a number of factors typically have a significant impact on the clinical outcome of a radial head implant. Four such factors, for example, are: biocompatibility of the implant; implant stiffness, which should be sufficient to prevent joint collapse under physiological loading; ability of the implant to restore correct head height and tissue balance and prevent gross changes in joint kinematics (i.e., a valgus laxity); and ability of the implant to minimize stress placed upon the capitellar articulation. It is therefore desirable for a radial head apparatus to be biocompatible, sufficiently stiff, allow for enough surgical flexibility to restore natural joint kinematics despite anatomical variations, and minimize the stress placed upon surrounding tissues.

SUMMARY

As disclosed herein, radial head implant apparatuses and methods are provided in accordance with the present matter wherein a shaft and a head portion can be axially movable within a stem portion.

It is an object of the present disclosure to provide novel radial head apparatuses and methods. An object having been stated above, and which is achieved in whole or in part by the present subject matter, other objects will become evident as the description proceeds when taken in connection with the accompanying drawings as best described hereinbelow.

BRIEF DESCRIPTION OF THE DRAWINGS

FIG. 13A of the drawings is a top perspective view of another embodiment of a radial head implant according to the present disclosure where the shaft can be locked in position with the stem portion with a spacer;

FIG. 13B of the drawings is an exploded perspective view of the radial head implant shown in FIG. 13A;

FIG. 13C of the drawings is a bottom perspective view of the shaft shown in FIG. 13B;

FIG. 13D of the drawings is a top plan view of the radial head implant shown in FIG. 13A;

FIG. 13E of the drawings is a cross-sectional view of the radial head implant shown in FIGS. 13A, 13B, 13C and 13D drawn along line E-E of FIG. 13D.

DETAILED DESCRIPTION

Figure 4:
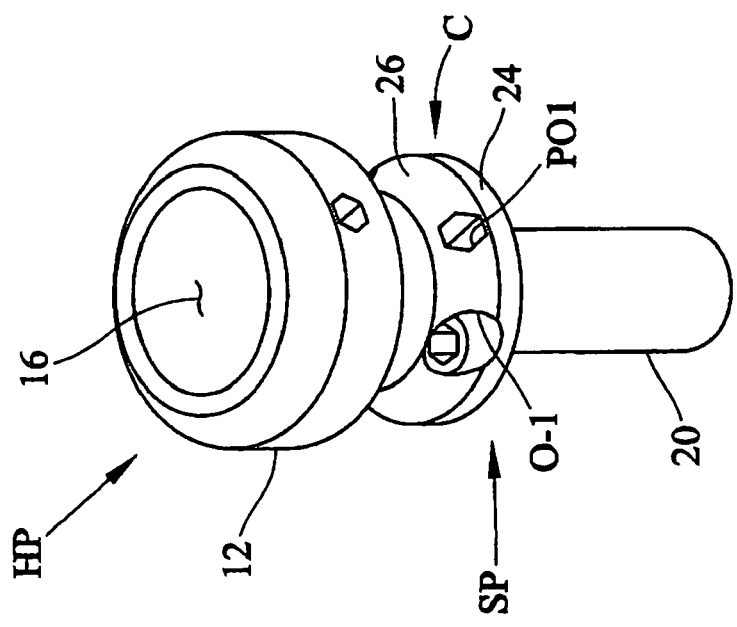
FIG. 4 of the drawings is a top perspective view of the radial head implant illustrated in the previous figures.

In accordance with the present disclosure, novel radial head implant apparatuses and methods are provided. Referring to the various figures of drawings, one embodiment of a radial head implant, generally designated 10, is illustrated and can include an upper head portion generally designated HP and a lower stem portion generally designated SP. As best shown in the cross-sectional views illustrated in FIGS. 2A and 2B of the drawings, head portion HP can comprise an outer shell 12 and an inner insert 14 which can fit within outer shell 12 and can be surrounded by outer shell 12 as shown with the bottom or lower side of inner insert 14 exposed as shown. The lower surface of inner insert 14 can comprise a non-horizontal or slanted surface as shown wherein the lower surface can slant or taper radially upwardly from the center of the lower surface of inner insert 14. Outer shell 12 can have an upper surface 16, best illustrated in FIGS. 2A, 2B and 4, which can be a smooth, concave articulating surface for articular engagement with a capitulum of a humerus bone. As known to those of skill in the art, the capitulum is a small, spheroidal projection on the distal end of the humerus which articulates with the radial head in a normal anatomical function. Any suitable material of construction, such as a ceramic material or implantable grade metals, for example a cobalt-chromium alloy or stainless steel, can be utilized for outer shell 12. Inner insert 14 can comprise a non-metal material of construction, such as for example a plastic component made from ultra-high-molecular-weight polyethylene (UHM-WPE). Inner insert 14 can define a recessed area 18, best shown in FIGS. 2A, 2B and 5, for receiving and engaging an upper portion of a shaft as described further below. Outer shell 12 and inner insert 14 can be designed such that the inner insert 14 can be rigidly fitted into the outer shell 12 and can even be pre-assembled in that configuration before being provided to an end user.

As shown particularly in FIGS. 1, 2A, 2B, 4, 6 and 8 of the drawings, stem portion SP can engage a radius bone as stem portion SP can comprise an elongated portion 20 which can be at least substantially cylindrical or tubular in shape with a smooth exterior for placement in the intermedullary canal of a radius bone as further described below. It is envisioned according to the present disclosure, however, that elongated portion 20 of stem portion SP could have an outer surface which is intentionally roughened or coated with a material to facilitate boney ingrowth and rigid fixation. For example, in instances where it may be desirable to have radial head implant 10 solidly affixed, such as by cement, to a radius bone, elongated portion 20 of stem portion SP would have an outer surface which is intentionally rough. Stem portion SP can further comprise a collar generally designated C at a proximal end thereof which can abut the end face of a contoured radius bone when elongated portion 20 of stem portion SP is in place in a radius bone. Collar C, also shown in FIG. 3 in addition to FIGS. 1, 2A, 2B, 4, 6 and 8, can be of an at least substantially annular shape and can be of a greater width than the width of elongated portion 20 of stem portion SP. The portion of collar C which extends away from elongated portion 20 has a lower surface 22 which can be perpendicular to elongated portion 20 and is adapted for abutting the end face of a contoured radius bone when stem portion SP is fully implanted. Collar C can also comprise an outer wall 24 which can be perpendicular with respect to lower surface 22.

Extending up from outer wall 24, collar C can comprise a tapered wall 26 which can intersect with an upper surface 28 of collar C. Upper surface 28 can be flat or otherwise structured for providing support to inner inert 14 of head portion HP when head portion HP is in a tilted position as shown in FIG. 2B with the lower surface of inner insert 14 resting against upper surface 28 of collar C.

An axial opening, generally designated 30 in FIGS. 2A and 2B, can be defined through a vertical axis of stem portion SP wherein axial opening 30 can receive a shaft as described below. Axial opening 30 can be defined through a center of upper surface 28 of collar C and extend axially through the center of elongated portion 20 of stem portion SP. Axial opening 30 can terminate short of the bottom of elongated portion 20 of stem portion SP such that axial opening 30 extends only partially, and not entirely, through the length of elongated portion 20. Any other suitable configuration and extent of axial opening 30 can also be used as can be appreciated by those of skill in the art. The material of construction for stem portion SP and collar C can be the same as for outer shell 12.

Radial head implant 10 can also comprise an interconnector mechanism for operatively connecting head portion HP with stem portion SP. As shown particularly in FIGS. 1, 2A, 2B, 3 and 7, the interconnector can be a shaft generally designated S for fitting at least partially within axial opening 30 of stem portion SP so as to be capable of axial or telescopic movement up and down within axial opening 30. An upper end 32 of shaft S can be formed into or include a smooth, upper end of suitable configuration, such as an at least substantial ball shape as shown. Recessed area 18 of inner insert 14 can be shaped or configured in an at least substantially identical, corresponding shape as upper end 32 as illustrated particularly in FIGS. 2A and 2B of the drawings. In this manner, upper end 32 can be fitted into recessed area 18 of inner insert 14 and movement of head portion HP can be allowed as desired on shaft S. FIG. 2B provides one example of head portion HP in a tilted position on shaft S. Shaft S can define one or more grooves, scallops or other features, on a side thereof, such as scallops 34, which can be used to facilitate maintenance of a desired position of shaft S within axial opening 30. A set screw SS and a pin P shown partially in FIGS. 2A and 2B can also be used to help maintain the position of shaft S in axial opening 30. Shaft S can further define an elongated slot 36 on a side opposite from the side defining scallops 34.

The shaft and portions of the head portion can optionally be provided as a single, integral component of any suitable material, such as those previously described. FIG. 2C of the drawings illustrates as an example head portion HP' wherein the shaft, the inner insert, and the outer shell are all integral and constitute a single component. In this configuration, no movement of the outer shell and inner insert is allowed separate from the shaft since all three are integral. Shaft HP' could also just have the outer shell and inner insert as a single component with the shaft separate.

Figure 9B:
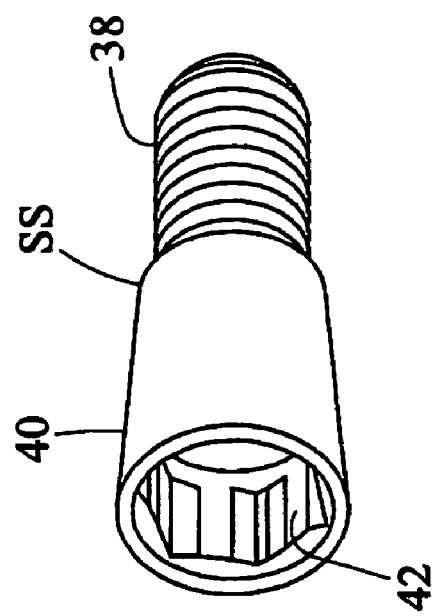
FIGS. 9A and 9B of the drawings are side and perspective views, respectively, of a set screw for use with the radial head implant illustrated in the previous figures.
Figure 9A:
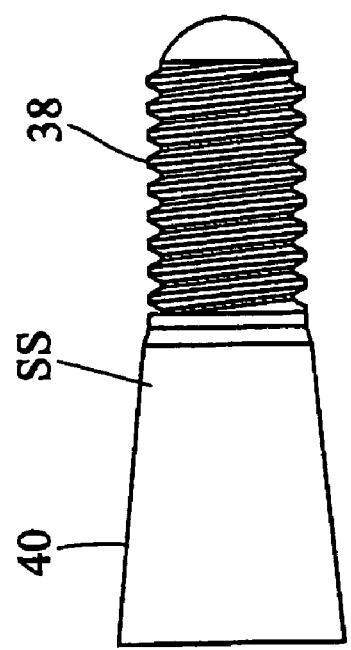

Shaft S can be moved within axial opening 30 of stem portion SP to a desired position and locked in place by use of set screw SS and pin P. To facilitate locking of shaft S and as shown for example in FIGS. 2A, 2B, 3, 6 and 8, collar C can define an opening O-1 that can communicate with axial opening 30 and can receive set screw SS. Opening O-1 can be at least partially threaded on the inside in order to threadably engage set screw SS. As illustrated in the various drawings, opening O-1 is preferably defined in an offset manner from the center of axial opening 30 such that set screw SS can be screwed into position within opening O-1 and contact an adjacent scallop 34 of shaft S in order to maintain a desired vertical position of shaft S within axial opening 30. As particularly shown in FIG. 3, opening O-1 can include an at least partially tapered, non-threaded and smooth proximate interior surface and a threaded distal interior surface for receiving and contacting set screw SS. For matingly engaging opening O-1, set screw SS can comprise, as particularly illustrated in FIGS. 9A and 9B, a threaded portion 38 proximate and/or at the distal end of set screw SS and a non-threaded and smooth, tapered portion 40 proximate and/or at the proximate end of set screw SS. A driving opening 42 can be defined in the proximate end of set screw SS as best shown in FIG. 9B for receiving a driver for driving screw 36. Driving opening 42 can be of any suitable configuration, such as hexagonal, adapted for receiving a driver for driving set screw SS.

Figure 1:
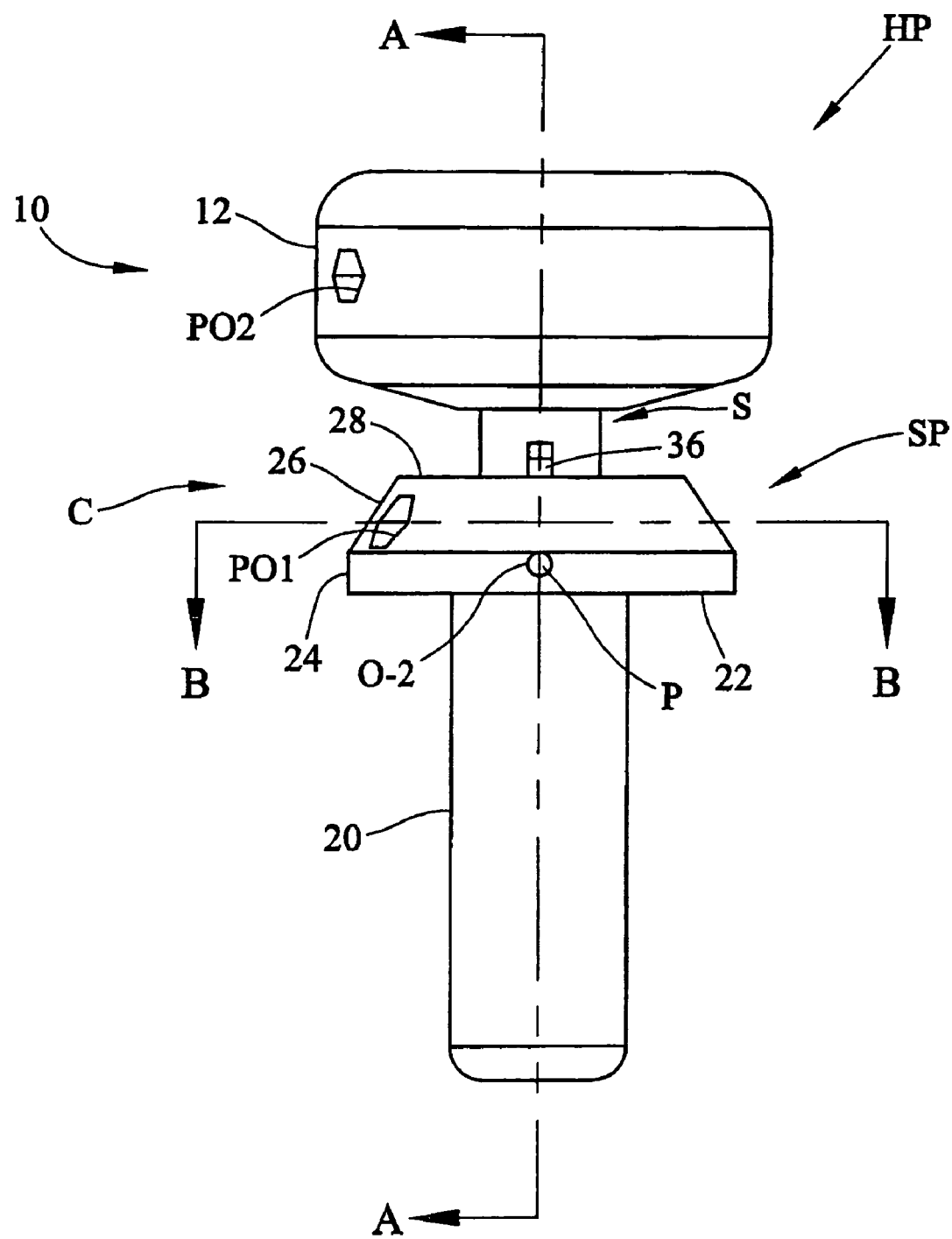
FIG. 1 of the drawings is a side elevation view of a radial head implant apparatus according to the present disclosure.
Figure 2A:
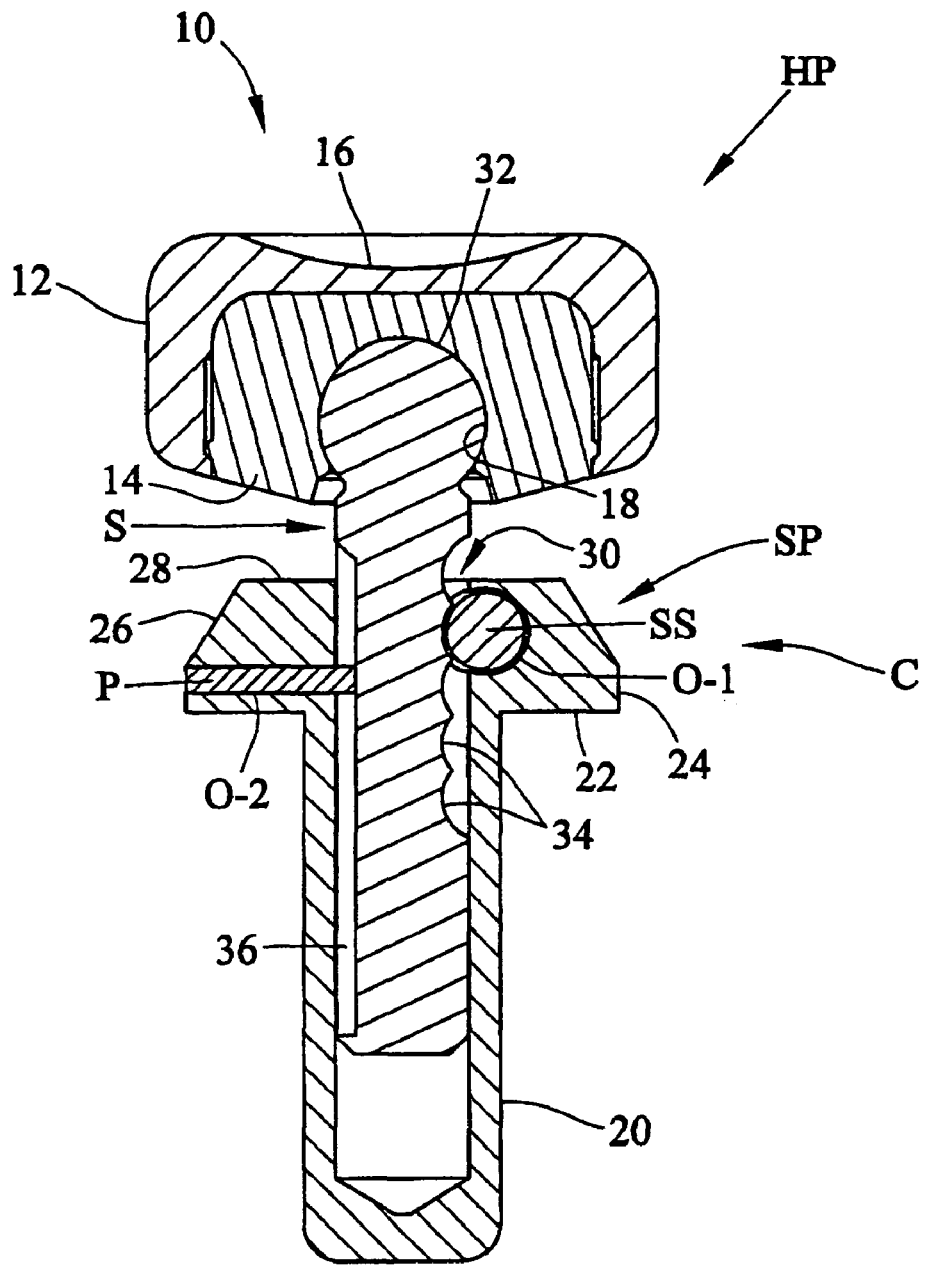
FIGS. 2A and 2C of the drawings are cross-sectional views of the radial head implant of FIG. 1 drawn along line A-A of FIG. 1.
Figure 2B:
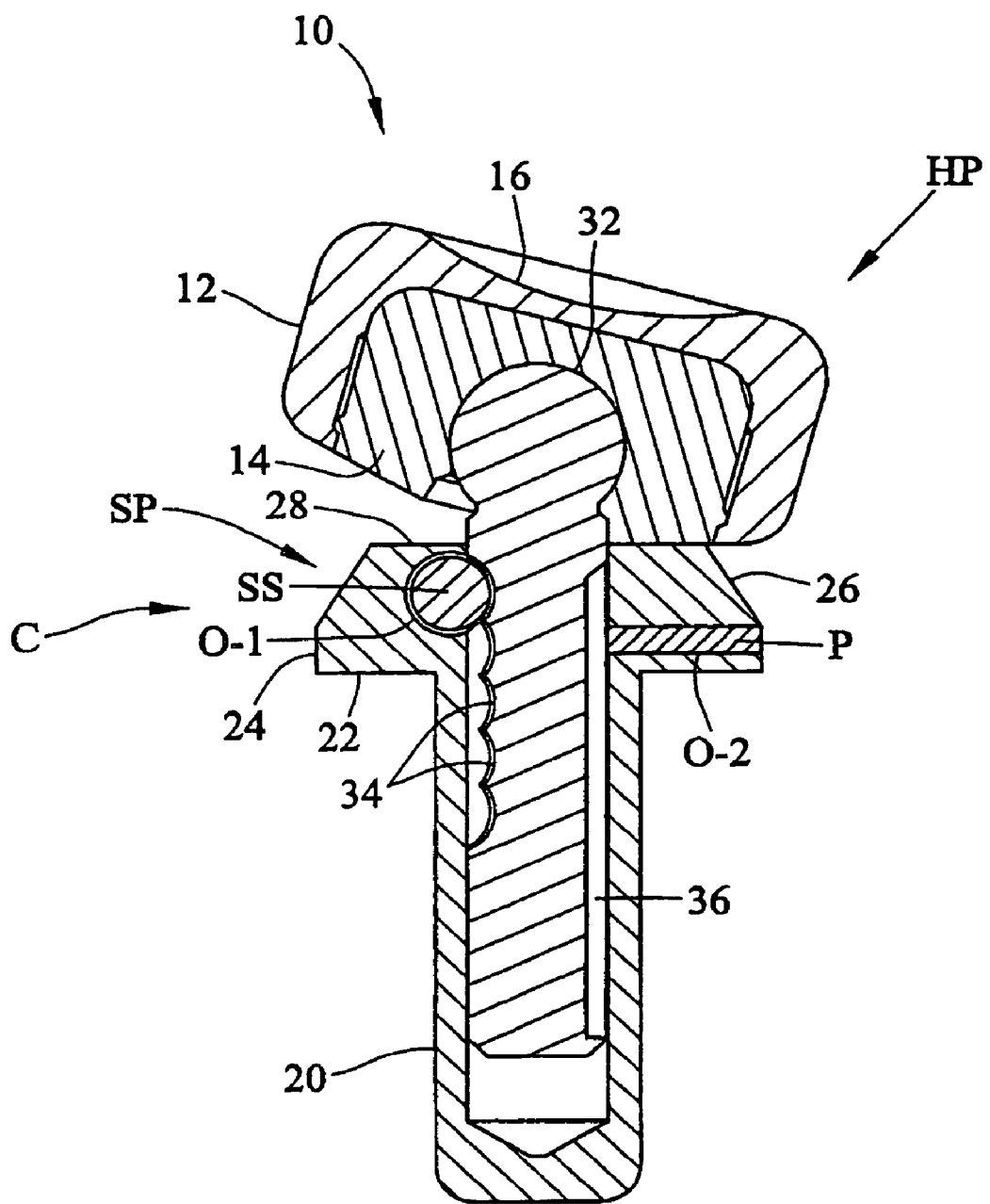
FIG. 2B of the drawings is a reverse cross-sectional view of the radial head implant shown in FIG. 2A.
Figure 2C:
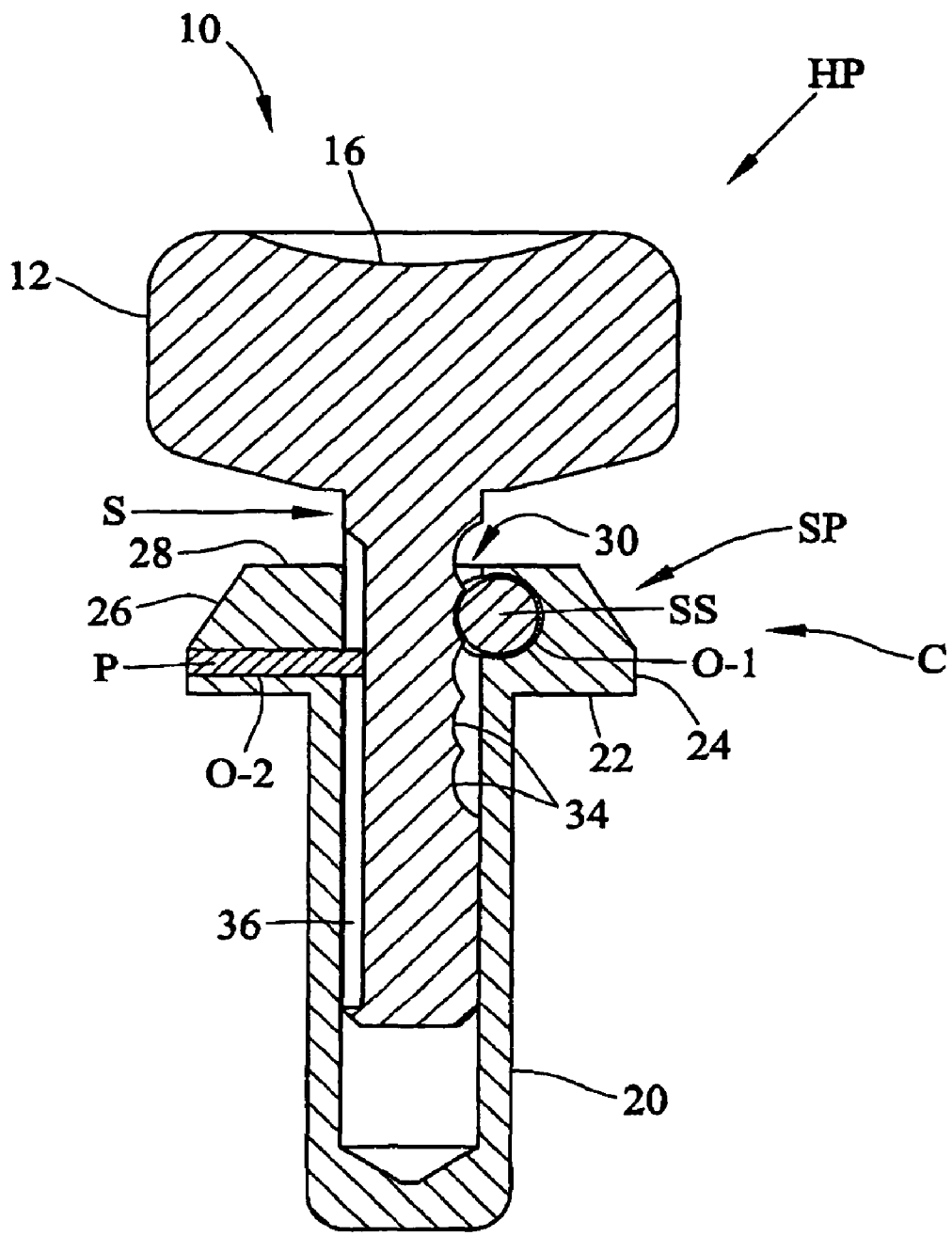
Figure 3:
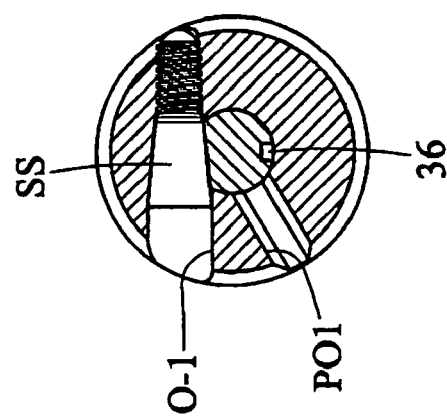
FIG. 3 of the drawings is a cross-sectional view of the radial head implant of FIG. 1 drawn along line B-B of FIG. 1.
Figure 8:
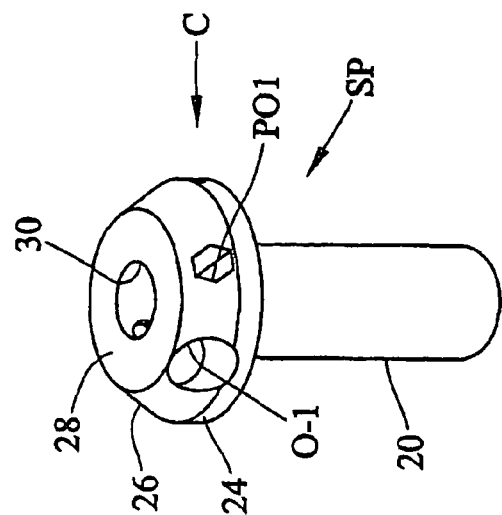
FIG. 8 of the drawings is a an isolated perspective view of the stem portion of the radial head implant illustrated in the previous figures.
Figure 7:
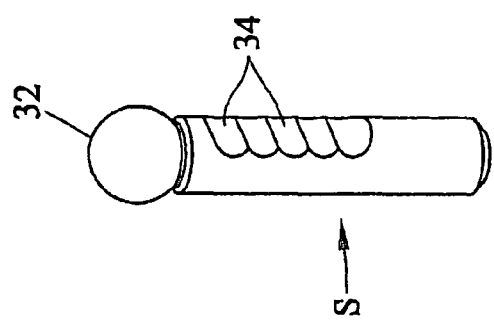
FIG. 7 of the drawings is an isolated, perspective view of the shaft of the radial head implant illustrated in the previous figures.
Figure 6:
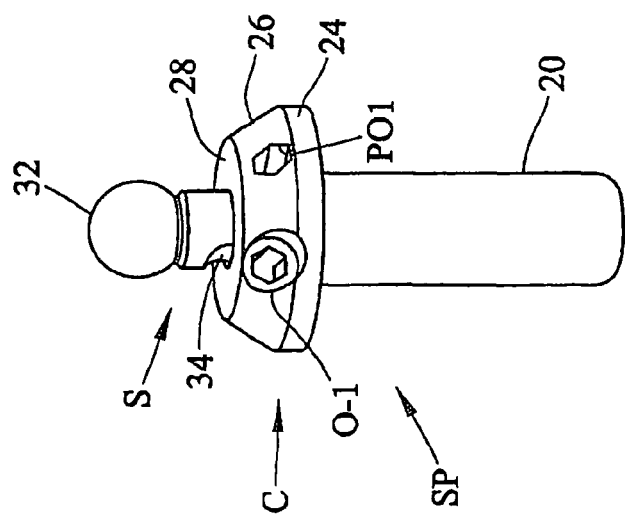
FIG. 6 of the drawings is a perspective view of a stem portion with a shaft of the radial head implant at least partially positioned within the stem portion.

Collar C can also define an opening O-2 as best illustrated in FIGS. 1 and 2A, 2B that can communicate with axial opening 30 and can receive pin P. In addition to set screw SS, pin P can be used to facilitate maintenance of shaft S in position within axial opening 30 of stem portion SP. Pin P can be positioned within opening O-2 which extends from outer wall 24 of collar C all the way to and communicates with axial opening 30 so that pin P can slide freely into slot 36 of shaft S. This feature can help shaft S stay in a desired left to right rotational position within axial opening 30 of stem portion SP and help ensure that the scallops also defined on another portion of shaft S line up appropriately for contact against set screw SS.

Figure 5:
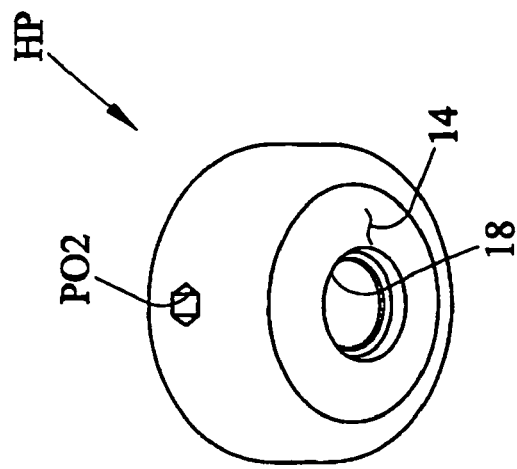
FIG. 5 of the drawings is an isolated, bottom perspective view of a head portion of the radial head implant illustrated in the previous figures.

For use in placement of radial head implant 10 according to the present disclosure, collar C can also define a placement opening PO1 as shown best in FIGS. 1, 3, 4, 6, and 8. Placement opening PO1 can be defined in tapered wall 26 of collar C and extend therethrough all the way to axial opening 30 or terminate short of axial opening 30. Placement opening PO1 can receive a placement driver and can be of any suitable configuration such as, for example, hexagonal, as can be appreciated by those skilled in the art. Head portion HP can also define a placement opening PO2 as best shown in FIGS. 1 and 5 wherein placement opening PO2 is defined in outer shell 12. Placement opening PO2, like placement opening PO1, can also be of any suitable configuration such as, for example, hexagonal. Placement openings PO1 and PO2 can be used for properly fitting head portion HP onto shaft S as described further below.

As with outer shell 12, the components of construction for the remaining components of radial head implant 10 can typically be made from implantable grade materials, such as for example, cobalt-chromium alloy or stainless steel. Generally, and as can appreciated by those of skill in the art, stem portion SP, shaft S and the locking components of set screw SS and pin P can all be made of the same material to prevent any galvanic corrosion issues. As noted previously, inner insert 14 of head portion HP can be made from ultra-high-molecular-weight polyethylene (UHMWPE).

Referring now to FIGS. 10A-10F of the drawings, progressive steps which can be associated with placement of radial head implant 10 are illustrated. These steps are illustrated and described herein for exemplary purposes and are not meant to be exhaustive of those which can could be taken in implanting radial head implant 10.

Figure 10A:
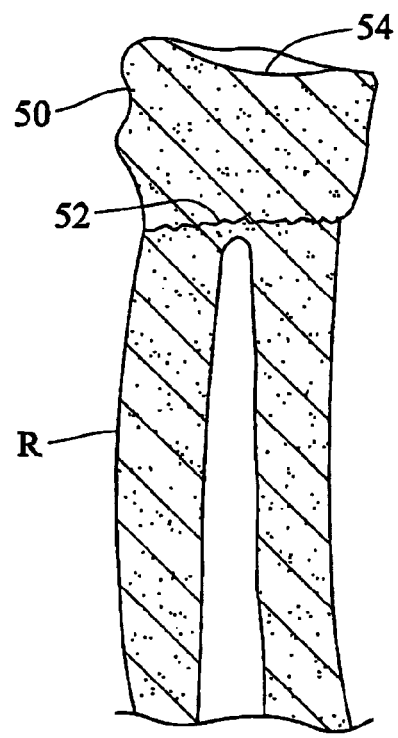
FIGS. 10A-10F of the drawings are sectional views illustrating progressive steps in placement of a radial head implant in a radius bone.
Figure 10B:
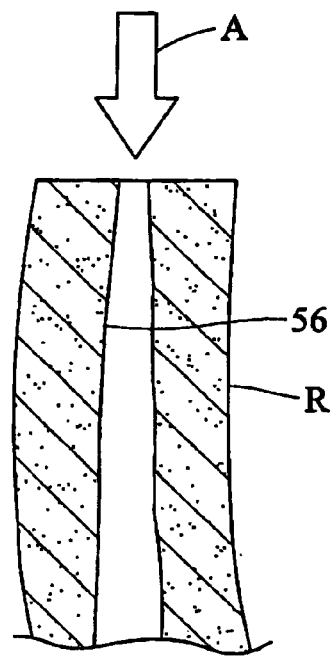
Figure 10C:
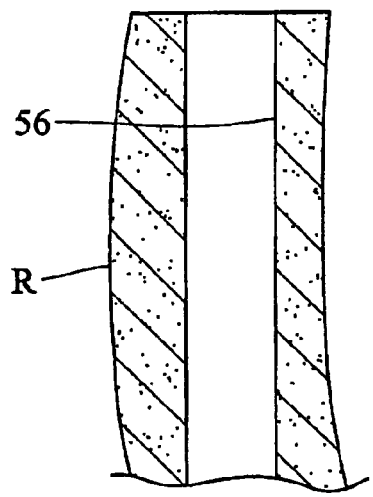
Figure 10D:
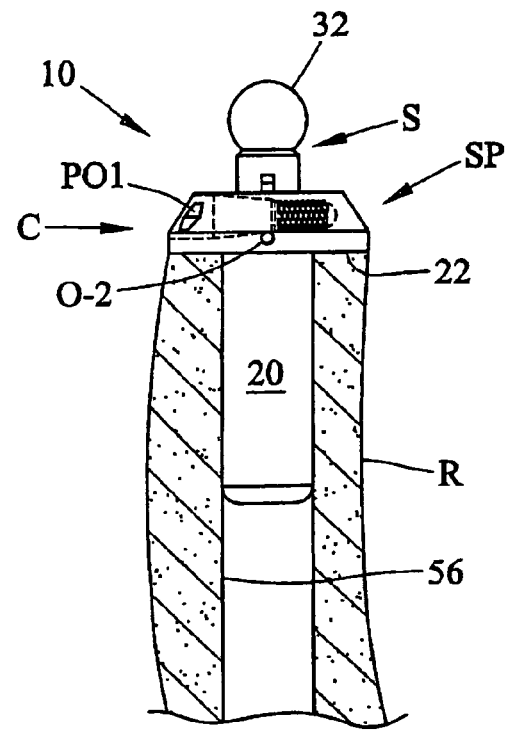

A radius bone R is shown in FIG. 10A with a radial head 50 that has a fracture as illustrated by fracture line 52 which traverses radial head 50. The upper surface 54 of radial head 50 is adapted for receiving a capitulum of a humerus bone. Fractured radial head 50 can be removed from radius bone R by a cutting or other suitable technique to remove the fractured bone portion preferably at a level below fracture line 52. Such removal can result in radius bone R as shown in FIG. 10B wherein the intermedullary canal 56 of radius bone R has been cut across and exposed. Next, intermedullary canal 56 of radius bone R can be suitably drilled or broached in the direction of arrow A to create an expanded intermedullary canal 56 as shown in FIG. 10C that can receive stem portion SP of radial head implant 10. As shown in FIG. 10D, elongated portion 20 of stem portion SP of radial head implant 10 can now be placed into expanded intermedullary canal 56. Lower surface 22 of collar C can abut the cut end of radius bone R once radial implant 10 is fully fitted into expanded intermedullary canal 56 as shown. Shaft S can be positioned, preferably without locking, into stem portion SP (into axial opening 30 as described previously) either before or after placement of stem portion SP in radius bone R.

After full placement of elongated portion 20 of stem portion SP into intermedullary canal 56 of radius bone R, the position of shaft S can be adjusted as needed and locked into position by fully screwing in set screw SS into opening O-1 of collar C. Pin P can be used to facilitate the locking by inserting pin P into opening O-2 of collar C. It is envisioned for manufacturing that pin P can be preassembled into stem portion SP by a manufacturer whereby an end user would not need to assemble it. Pin P can prevent shaft S from rotating in stem portion SP, and potentially blocking set screw SS from insertion, while the height of shaft S is appropriately set as desired. After this, set screw SS locks both the rotational position and the vertical position of shaft S within stem portion SP.

Figure 10E:
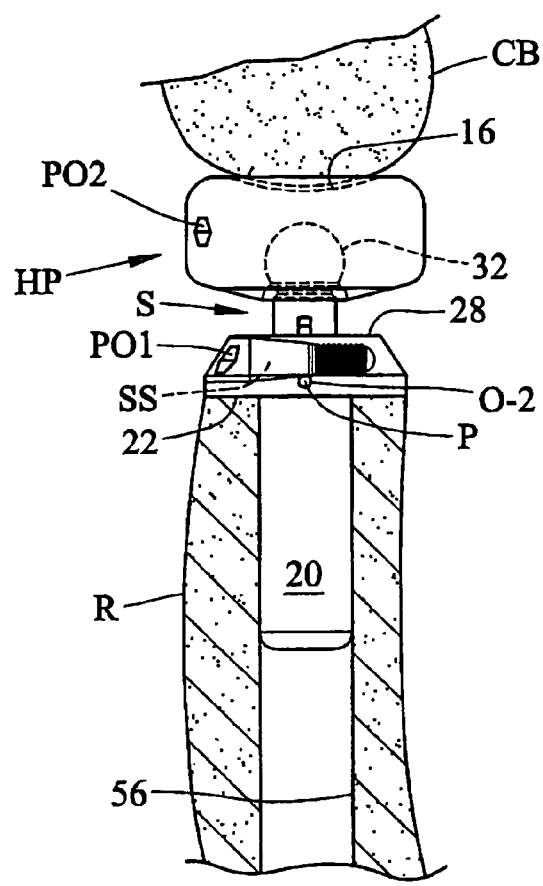
Figure 10F:
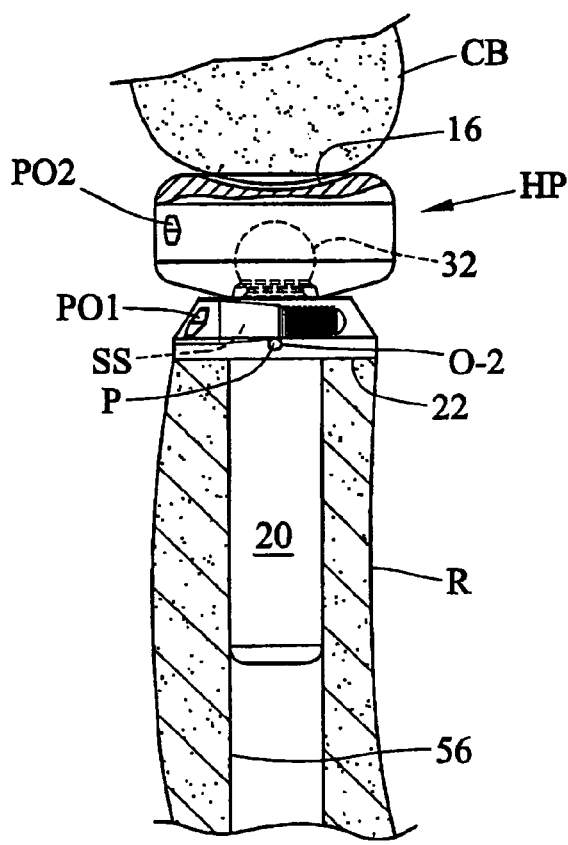

Previous or subsequent to locking of shaft S in position in stem portion SP, head portion HP of radial head implant 10 can be attached to shaft S. To attach head portion HP, head portion HP can be positioned above upper end 32 of shaft S below a capitulum bone CB of a humerus bone as shown in FIG. 10E. To fit upper end 32 of shaft S into recessed area 18 of inner insert 14 of head portion HP, a placement driver (not shown) can be placed into placement opening PO1 (not shown in FIG. 10A-10F) of collar C and another placement driver can be placed into placement opening PO2 of head portion HP. The placement drivers can then be pinched together to snap fit upper end 32 of shaft S into recessed area 18 of inner insert 14 to fit head portion HP onto shaft S. This feature facilitates proper placement of head portion HP onto shaft S since the proximity of capitulum CB can make proper fitting difficult without use of the placement drivers. Referring to FIG. 10F, shaft S can be adjusted even after placement of head portion HP as desired by use of set screw SS and pin P. The position of shaft S in stem portion SP has been lowered to its lowest position in FIG. 10F where head portion HP abuts upper surface 28 (FIG. 10E) and wherein shaft S is no longer exposed. Capitulum CB fits against upper surface 16 of head portion HP. Quite advantageously, the height of radial head implant 10 and/or the position of head portion HP, such as tilted or not tilted to any desired degree, can be adjusted for implantation. Also quite advantageously, the height of radial head implant 10 and/or the position of head portion HP can be adjusted after implantation without having to disengage radial head implant 10 from either the radius bone or the humerus bone, and therefore without having to remove radial head implant 10.

Figure 11C:
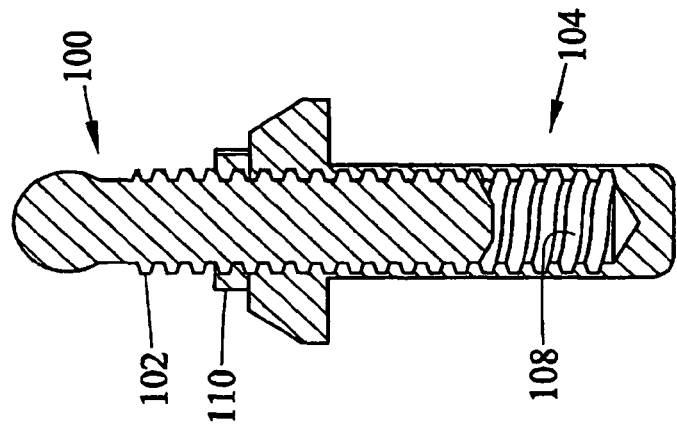
FIGS. 11A and 11B of the drawings are top perspective views and FIG. 11C is a vertical cross-sectional view of another embodiment of a radial head implant according to the present disclosure where the shaft can threadably engage the stem portion.
Figure 11B:
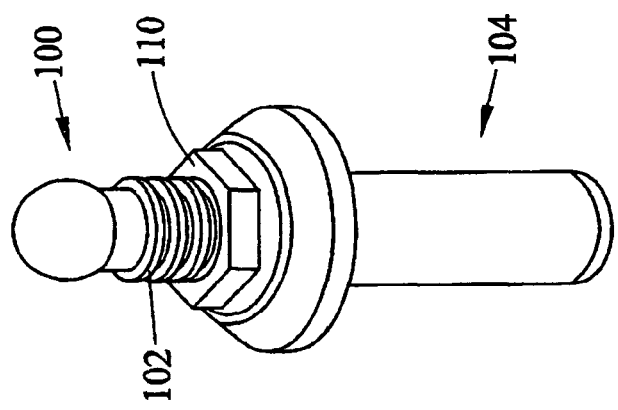
Figure 11A:
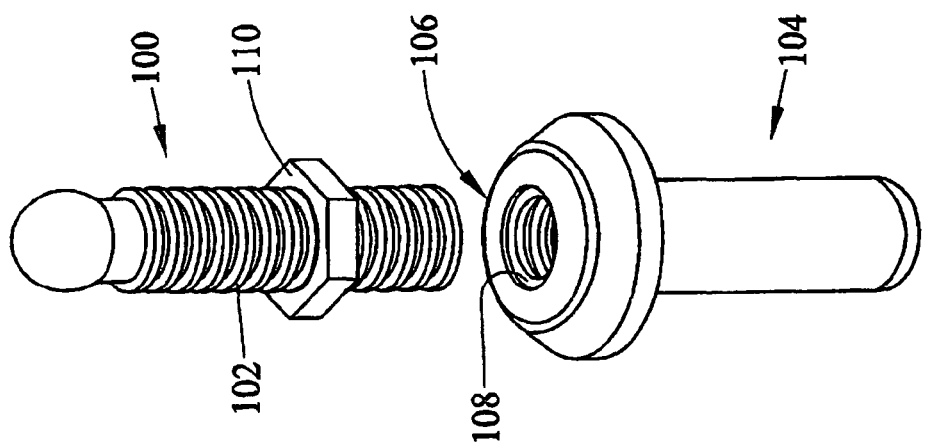

FIGS. 11A-11C of the drawings provide various illustrations of a shaft and stem portion of a radial head implant according to the present disclosure that can be used with any type of head portion described previously and where no set screw or pin is needed to maintain the shaft in a desired position within the stem portion. As shown, generally designated shaft 100 can be at least partially threaded, such as for example with threads 102, on its outer perimeter, and generally designated stem portion 104 can have an axial opening 106 that is at least partially threaded, such as for example with threads 108, on its inner perimeter for matingly engaging and threadably receiving shaft 100. Any suitable fastener or locking member can be used to lock shaft 100 into a position in stem portion 102, such as for example a lock nut 110. In this configuration, desired positioning of shaft 100 within stem portion 104 can be accomplished by simply screwing shaft 100 into and out of axial opening 106 of stem portion 104.

Figure 12B:
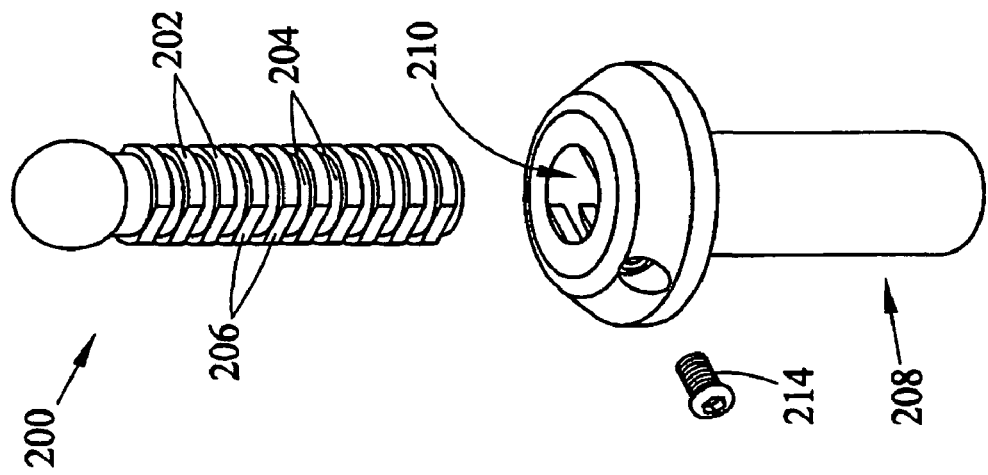
FIG. 12B of the drawings is an exploded perspective view of the radial head implant shown in FIG. 12A.
Figure 12A:
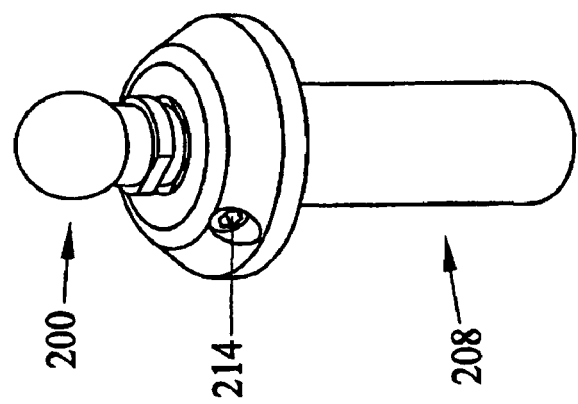
FIG. 12A of the drawings is a top perspective view of another embodiment of a radial head implant according to the present disclosure where the shaft can be locked in position in the stem portion by rotation of the shaft.
Figures 12C, 12D, 12E:
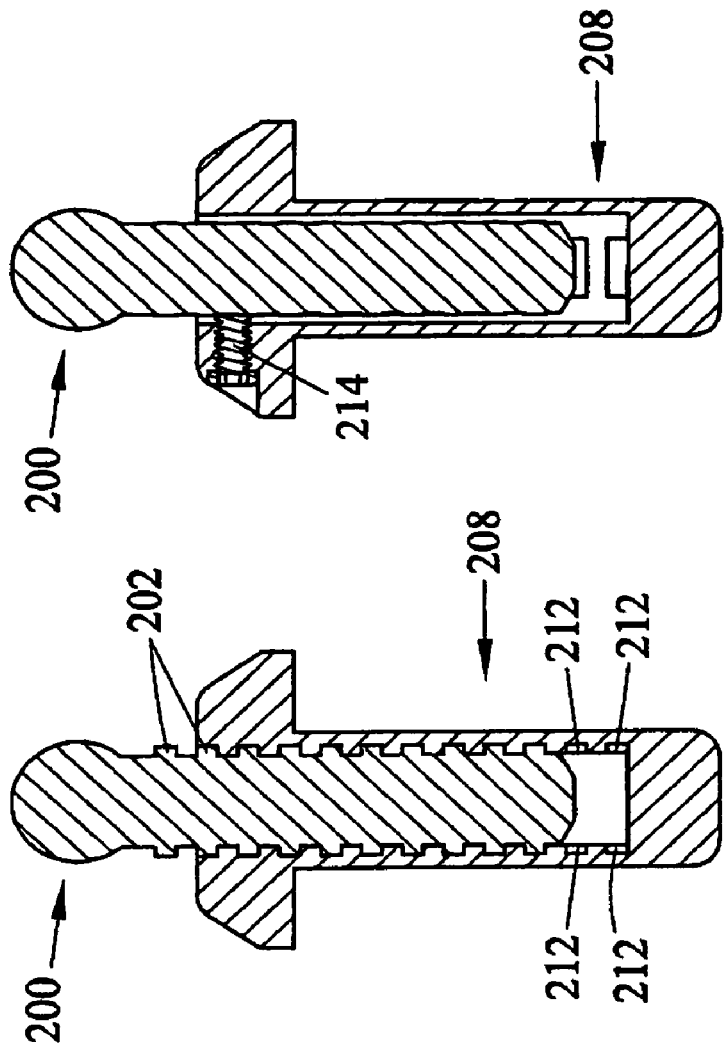
FIG. 12C of the drawings is a top plan view of the radial head implant shown in FIG. 12A.
FIGS. 12D of the drawings is a cross-sectional view of the radial head implant shown in FIGS. 12A, 12B and 12C drawn along line C-C of FIG. 12C.
FIG. 12E of the drawings is a cross-sectional view of the radial head implant shown in FIGS. 12A, 12B and 12C drawn along line D-D of FIG. 12C.

FIGS. 12A-12E of the drawings provide various illustrations of another embodiment of a shaft and stem portion of a radial head implant according to the present disclosure that can be used with any type of head portion described previously. As shown, generally designated shaft 200 can comprise one or more radial extensions, such as for example radial extensions 202, disposed at least partially on the outer surface of shaft 200. Radial extensions 202 can be disposed as shown on opposite sides of the outer surface of shaft 200 and spaced apart vertically so as to form grooves, such as for example grooves 204. Surfaces 206 that are horizontally between radial extensions 202 on opposing sides of shaft 200 can be less radially extended than radial extensions 202 or have no radial extensions. Generally designated stem portion 208 can have an axial opening generally designated 210 that can define grooves, such as for example grooves 212, at least partially disposed along certain portions of the inner surface of axial opening 210. FIGS. 12D and 12E of the drawings illustrate different cross-sectional views of shaft 200 positioned partially in axial opening 210 of stem portion 208. As shown in FIG. 12D, shaft 200 is rotationally oriented such that radial extensions 202 are positioned within and engaged with grooves 212 of axial opening 210. Shaft 200 cannot be vertically moved within axial opening 210 in this position. A set screw 214 can be used and positioned through stem portion 208 against shaft 200, such as for example against one or more surfaces 206, as shown in FIG. 12E to lock shaft 200 in place within axial opening 210 so that shaft 200 cannot be moved rotationally. It can be understood that once set screw 214 is loosened or removed, shaft 200 can be rotated left or right to move radial extensions 202 out of grooves 212 of axial opening 210 whereby shaft 200 can then be moved vertically within axial opening 210 as desired. Once shaft 200 has been moved to a desired vertical position, shaft 200 can then be rotated again to move radial extensions 202 into alignment with and in grooves 212 of axial opening 210 to again lock shaft 200 into another vertical position. Set screw 214 can then be tightened to lock shaft 200 in place so that shaft 200 cannot be moved rotationally.

FIGS. 13A-13E of the drawings provide various illustrations of another embodiment of a shaft and stem portion of a radial head implant according to the present disclosure that can be used with any type of head portion described previously. As shown, a spacer generally designated 300 can be used and positioned between a shaft generally designated 302 and a stem portion generally designated 304 with an axial opening generally designated 306. Spacer 300 can be of any suitable shape or configuration and material of construction. As shown for example in FIGS. 13A-13E, spacer 300 can be at least generally disc shaped with a cutaway center that can be open to a side of spacer 300. Spacer 300 can define one or more slots and/or protrusions on its upper and/or lower surfaces for engagement with a collar 308 of stem portion 304. As shown in one example, spacer 300 can have slots such as slots 310 on the upper surface of spacer 300, and spacer 300 can have protrusions such as protrusions 312 on the bottom surface of spacer 300, as particularly shown in FIGS. 13A and 13E of the drawings. As particularly shown in FIGS. 13C and 13E, shaft 302 can have a shaft collar 314 that can comprise protrusions such as protrusions 316 on the bottom surface of shaft collar 314 such that protrusions 316 can slide into and out of slots 310 on spacer 300. Similarly, collar 308 of stem portion 304 can have slots such as slots 318 on its upper surface such that protrusions 312 of spacer 300 can slide into and out of slots 318. It can be understood then that spacer 300 can be used to lock shaft 302 into position in axial opening 306 where axial or telescopic movement of shaft 302 is prevented. It is envisioned that more than one spacer 300 could be utilized, such as for example in a stacked assembly of spacers. Additionally, spacers of different thicknesses and sizes can be utilized as desired for shaft 300 to be placed and locked in various positions within axial opening 306.

It will be understood that various details of the presently disclosed subject matter may be changed without departing from the scope of the subject matter. Furthermore, the foregoing description is for the purpose of illustration only, and not for the purpose of limitation.

What is claimed is:

1. An implant for engaging a radius bone and a humerus bone, the implant comprising:
   (a) a head portion comprising an upper surface for articular engagement with a capitulum of a humerus bone and a lower surface;
   (b) a stem portion for engagement with a radius bone and defining an axial opening;
   (c) a shaft having an upper shaft portion for engagement within an area of engagement in the lower surface of the head portion, the shaft having a lower, elongated shaft portion for slidable engagement with the stem portion by the elongated shaft portion fitting into the axial opening of the stem portion whereby the elongated shaft portion is axially movable within the axial opening of the stem portion;
   (d) a collar at a proximal end of the stem portion defining an opening with an axis at least generally perpendicular to an axis of the axial opening of the stem portion, the opening of the collar being configured to receive a screw for preventing the shaft from sliding within the axial opening of the stem portion; and
   (e) wherein the head portion comprises an outer shell and an inner insert, and wherein the area of the head portion for engagement with the upper shaft portion is a recessed area within the inner insert.

2. The implant of claim 1 wherein the insert is removably positioned within the outer shell.

3. An implant for engaging a radius bone and a humerus bone, the implant comprising:
   (a) a head portion comprising an upper surface for articular engagement with a capitulum of a humerus bone and a lower surface;
   (b) a stem portion for engagement with a radius bone and defining an axial opening;
   (c) a shaft having an upper shaft portion for engagement with the lower surface of the head portion, the shaft having a lower, elongated shaft portion for slidable engagement with the stem portion by the elongated shaft portion fitting into the axial opening of the stem portion whereby the elongated shaft portion is axially movable within the axial opening of the stem portion; and
   (d) a collar at a proximal end of the stem portion defines an opening with an axis at least generally perpendicular to an axis of the axial opening of the stem portion, the opening of the collar comprises an at least partially threaded, distal wall portion and a smooth, tapered, proximate wall portion connecting with an outer surface of the collar.

4. A radial head implant for engaging a radius bone and a humerus bone, the radial head implant comprising:
   (a) a head portion comprising an outer shell and an inner insert fitted into the outer shell, the outer shell having an upper surface for articular engagement with a capitulum of a humerus bone, and the inner insert having a recessed area on a lower surface of the inner insert;
   (b) a stem portion for engagement with a radius bone, the stem portion comprising a collar at a proximal end of the stem portion and comprising an elongated portion below the collar, the stem portion defining an axial opening though a central axis of the stem portion;
   (c) a shaft having an upper shaft portion with an upper end for fitting at least partially into the recessed area of the inner insert, and the shaft having a lower, elongated shaft portion for slidable engagement within the axial opening of the stem portion by the elongated shaft portion fitting into the axial opening of the stem portion whereby the elongated shaft portion is axially movable within the axial opening; and
   (d) the collar at the proximal end of the stem portion defining an opening with an axis at least generally perpendicular to the central axis of the axial opening of the stem portion, the opening of the collar being configured to receive a screw that prevents the shaft from sliding within the axial opening of the stem portion.

5. The implant of claim 4 wherein the head portion and the shaft are integral.

* * * * *